(12) United States Patent
Hanby

(10) Patent No.: US 9,448,220 B2
(45) Date of Patent: Sep. 20, 2016

(54) SPECTROMETRIC DEVICE FOR THE ANALYSIS OF ENVIRONMENTAL AND GEOLOGICAL SAMPLES

(71) Applicant: HANBY INTERNATIONAL, LLC, Houston, TX (US)

(72) Inventor: John David Hanby, Katy, TX (US)

(73) Assignee: Charles D. Fator, Houston, TX (US)

(*) Notice: Subject to any disclaimer, the term of this patent is extended or adjusted under 35 U.S.C. 154(b) by 0 days.

(21) Appl. No.: 14/373,295

(22) PCT Filed: Jan. 18, 2013

(86) PCT No.: PCT/US2013/022263
§ 371 (c)(1),
(2) Date: Jul. 18, 2014

(87) PCT Pub. No.: WO2013/109964
PCT Pub. Date: Jul. 25, 2013

(65) Prior Publication Data
US 2015/0004714 A1 Jan. 1, 2015

Related U.S. Application Data

(63) Continuation-in-part of application No. 13/352,629, filed on Jan. 18, 2012.

(51) Int. Cl.
*G01N 33/24* (2006.01)
*G01N 33/00* (2006.01)
(Continued)

(52) U.S. Cl.
CPC ............ *G01N 33/241* (2013.01); *B32B 37/02* (2013.01); *B32B 37/06* (2013.01); *B32B 37/10* (2013.01); *B32B 37/22* (2013.01); *G01N 21/78* (2013.01); *G01N 21/8483* (2013.01);
(Continued)

(58) Field of Classification Search
CPC ....... B32B 37/02; G01N 33/00; G01N 30/74
USPC .............. 422/62, 68.1, 82.05, 78, 63, 82.06; 156/301, 306.6; 436/139, 164, 178; 502/159
See application file for complete search history.

(56) References Cited

U.S. PATENT DOCUMENTS 4,992,379 A 2/1991 Hanby
5,686,724 A 11/1997 Spilker et al.
(Continued)

FOREIGN PATENT DOCUMENTS

JP 2005164402 A 6/2005
WO 97/07393 A1 2/1997

OTHER PUBLICATIONS

Srirattnai et al., "Encapsulated AlCl3: A Convenient Catalyst for the Alkylation of Benzene with Dodecene," Tetrahedron Letters, 2002, vol. 43, pp. 4555-4557.
(Continued)

*Primary Examiner* — Dennis M White
*Assistant Examiner* — Bryan Kilpatrick
(74) *Attorney, Agent, or Firm* — Conley Rose, P.C.

(57) ABSTRACT

A system and method for analyzing contaminants such as hydrocarbons in soil and ground water utilizes a reaction device comprising a catalyst encapsulated in a permeable material and processes that device in contact with a contaminant in an analytical device in order to generate a spectrogram indicative of the contaminants in the soil and ground water.

20 Claims, 6 Drawing Sheets

(51) Int. Cl.

| | | |
|---|---|---|
| *G01N 30/74* | (2006.01) | |
| *G01N 21/78* | (2006.01) | |
| *G01N 21/84* | (2006.01) | |
| *G01N 35/02* | (2006.01) | |
| *G01N 35/00* | (2006.01) | |
| *B32B 37/02* | (2006.01) | |
| *B32B 37/06* | (2006.01) | |
| *B32B 37/10* | (2006.01) | |
| *B32B 37/22* | (2006.01) | |
| *G01N 1/40* | (2006.01) | |
| *G01N 35/10* | (2006.01) | |

(52) U.S. Cl.
CPC ............. *G01N 30/74* (2013.01); *G01N 33/00* (2013.01); *G01N 35/00009* (2013.01); *G01N 35/021* (2013.01); *B32B 2307/70* (2013.01); *B32B 2307/73* (2013.01); *B32B 2323/04* (2013.01); *B32B 2323/10* (2013.01); *B32B 2383/00* (2013.01); *B32B 2581/00* (2013.01); *G01N 2001/4061* (2013.01); *G01N 2035/023* (2013.01); *G01N 2035/1032* (2013.01); *Y10T 156/1095* (2015.01); *Y10T 436/21* (2015.01)

(56) References Cited

U.S. PATENT DOCUMENTS

| | | |
|---|---|---|
| 5,834,655 A | 11/1998 | Lad et al. |
| 6,040,191 A * | 3/2000 | Grow .............................. 506/12 |
| 6,444,461 B1 | 9/2002 | Knapp et al. |
| 7,518,710 B2 * | 4/2009 | Gao et al. ....................... 356/73 |
| 2004/0121402 A1 | 6/2004 | Harper et al. |

OTHER PUBLICATIONS

International Search Report and Written Opinion dated May 15, 2013, for International Application No. PCT/US2013/022263, filed Jan. 18, 2013.
USPTO Office Action dated Apr. 1, 2014, for U.S. Appl. No. 13/352,629, filed Jan. 18, 2012.
USPTO Final Office Action dated Nov. 14, 2014, for U.S. Appl. No. 13/352,629 filed Jan. 18, 2012.

* cited by examiner

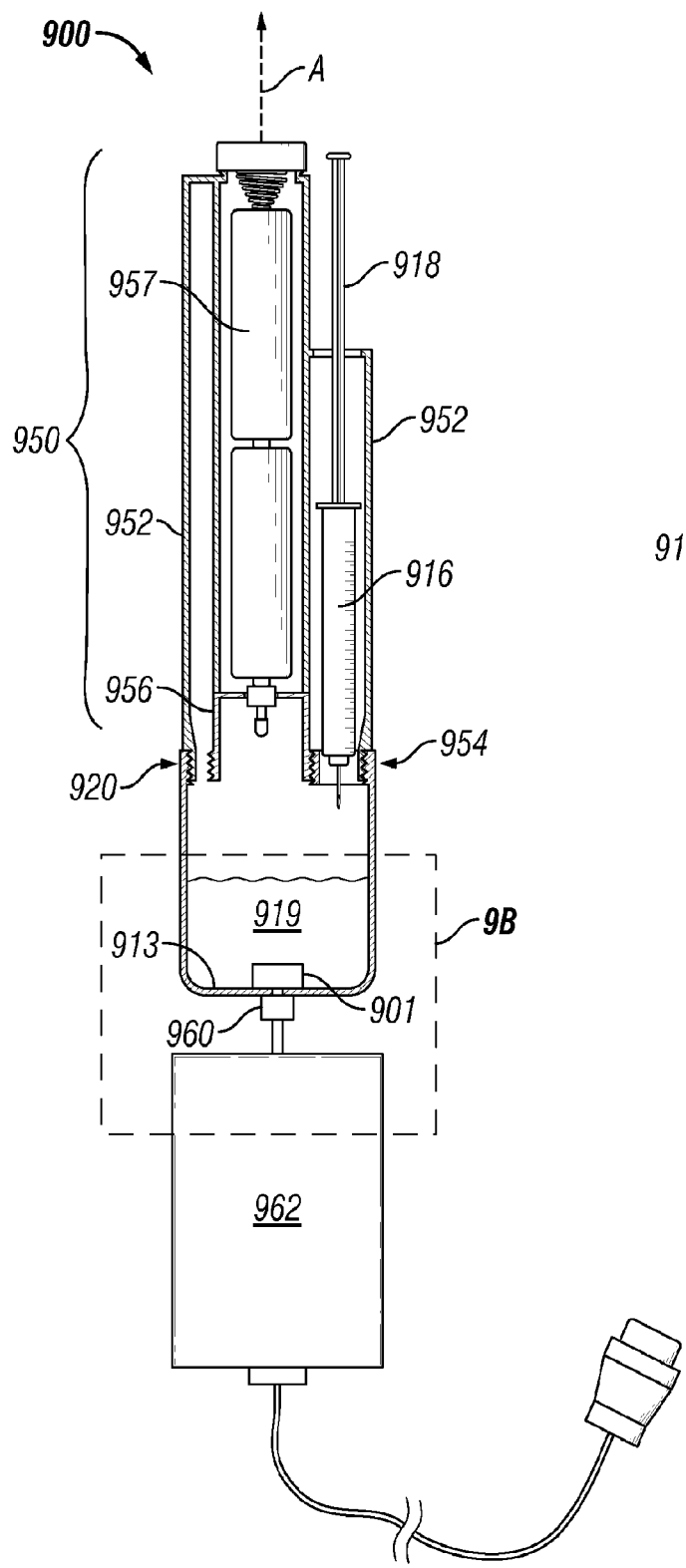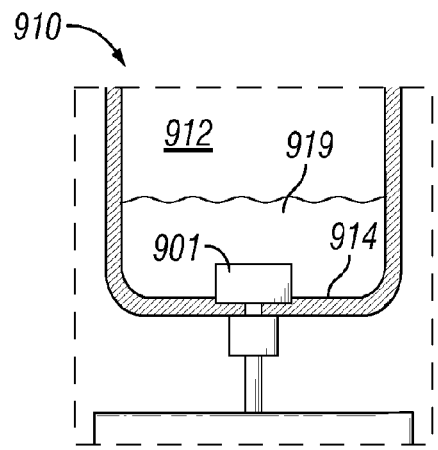
FIG. 9B
FIG. 9A

SPECTROMETRIC DEVICE FOR THE ANALYSIS OF ENVIRONMENTAL AND GEOLOGICAL SAMPLES

CROSS-REFERENCE TO RELATED APPLICATIONS

This application is a 35 U.S.C. §371 national stage application of PCT/US2013/022263 filed Jan. 18, 2013 and entitled "Spectrometric Device for the Analysis of Environmental and Geological Samples," which is a continuation in part of U.S. application Ser. No. 13/352,629 filed Jan. 18, 2012 and entitled "Diffusion/Chemical Reaction/Spectrometric Device for the Analysis of Petroleum Hydrocarbons in Environmental and Geological Formation Samples," both of which are hereby incorporated herein by reference in their entirety for all purposes.

STATEMENT REGARDING FEDERALLY SPONSORED RESEARCH OR DEVELOPMENT

Not applicable.

BACKGROUND

The present disclosure relates generally to the analysis of contaminants, particularly hydrocarbons, in environmental or geological samples. More specifically, the disclosure is directed to devices for spectrometric analysis of hydrocarbons. Generally, robust chromophores in the ultraviolet and visible regions of the electromagnetic spectrum may be produced by Friedel-Crafts Reactions, hereinafter FCRs, with a wide variety of the chemical constituents in crude oil and crude oil fractions. These chromophores may serve as spectral markers to form unique spectrograms or spectral fingerprints for the chemical components in a hydrocarbon or petroleum substance. These unique spectrograms may permit determination of the source of the hydrocarbon or petroleum substances. Still further, this fingerprinting of the petroleum substance may be used for information related to various environmental investigations and in the oil and gas exploration and production (E&P) industry.

Previously, the present inventor has sought to utilize FCR kits for detection of hydrocarbons in environmental and geological formation samples. Such kits were also used, for example, by the United States Department of Commerce "Rapid Commercialization Initiative" Program (1997) and selected as one of the "Ten Best Environmental Developments in the United States." Further, development of a prototype device in that configuration was laboratory and field tested by the Environmental Protection Agency and the U.S. Army Corps of Engineers Cold Regions Research and Engineering Laboratory.

However, in application these kits required the transportation of a plurality of liquid reagents into the field to conduct the tests. Additionally, the coloration of the result provides for the type of hydrocarbon and the concentration in the formation, based on the color and intensity of the reaction, but does not provide spectral fingerprinting and identification of the source of the contaminant. The present disclosure is directed to a device and method for spectrometric analysis of hydrocarbon contaminants in environmental and geological samples.

SUMMARY

Generally, the present disclosure relates to analyzing contaminants such as hydrocarbons in soil and ground water. The disclosure relates to a reaction device comprising a catalyst encapsulated in a permeable material and a method of manufacturing that device. Further, the disclosure relates to an analytical device configured for processing the reaction device in order to generate a spectrogram indicative of the contaminants in the soil and ground water. Also, the disclosure relates to a method of operating the analytical device.

A reaction device includes a first and a second portion of a permeable material sealably encapsulating an anhydrous Friedel-Crafts catalyst. The first and second portions of the permeable material are configured to form a linear tape having regularly spaced discrete reaction vessels retaining the Friedel-Crafts catalyst or a tab having individual vessels retaining the Friedel-Crafts catalyst. The first and second portions of the permeable material includes at least one non-reactive polymer chosen from the group consisting of olefinic polymers, silicon polymers, or hydrophobic polymers.

A method manufacturing a reaction device includes positioning an anhydrous catalyst reagent on a first portion of a material, overlaying a second portion of a material, sealing the second material to the first material, and finishing an encapsulated reaction device. The material may include at least one non-reactive polymer chosen from the group consisting of polyethylene, polypropylene, other olefinic polymers, silicon polymers, or hydrophobic polymers. Sealing the second material to the first material may include thermal sealing or pressure sealing. Finishing an encapsulated reaction device may include forming a linear tape having regularly spaced discrete reaction vessels retaining the Friedel-Crafts catalyst or forming individual, discrete tabs retaining the Friedel-Crafts catalyst.

A device for analyzing soil and water contaminants includes a chemical module, wherein the chemical module comprises an extraction vessel having a floor configured to retain a reaction device, walls configured to retain a solvent reservoir and a coupler, and an analysis module, wherein the analysis module comprises a body with a complementary coupler, a light source, a filter, an optical receptor, and an analysis device. The solvent reservoir may include a sample site. The body of the device may further include an extendible plunger configured to mechanically mix a solvent and a sample by disrupting the solvent reservoir to form an extract. The plunger may be configured to expose the reaction device to the extract. The reaction device may be configured to catalyze a Friedel-Crafts chromophore reaction in the extract. The light source may include a metal halide configured for illuminating the extract in a spectra of the Friedel-Crafts chromophore. The receptor may include an optical receptor configured for detecting the refracted or transmitted light in the extract.

A method for analyzing soil and water contaminants includes loading a reaction device having a Friedel-Crafts catalyst encapsulated in a permeable material, positioning a solvent reservoir adjacent the reaction device, mixing a sample and the solvent reservoir to form an extract, exposing the extract to the reaction device to form a Friedel-Crafts chromophore in the extract, illuminating the extract, collecting the refracted or transmitted light therethrough, and generating a spectrogram indicative of the soil and water contaminants.

BRIEF DESCRIPTION OF THE DRAWINGS

For a more complete understanding of the present disclosure, reference is now made to the following brief descrip

FIG. 9 illustrates an alternative configuration of a device for analyzing hydrocarbons in soil and water shown in FIG. 4.

DETAILED DESCRIPTION

Figure 1:
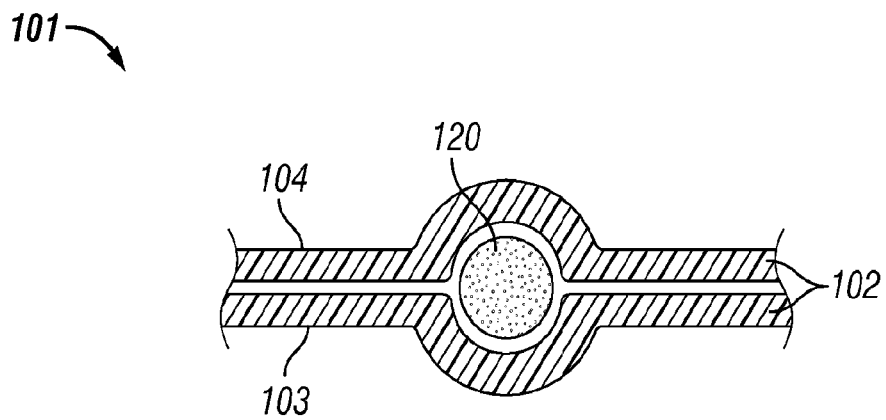
- FIG. 1 illustrates a reaction device having a Friedel-Crafts catalyst encapsulated in a material.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

Generally, the analytical spectral data produced by the disclosure herein is related to U.S. Pat. No. 4,992,379 previously granted to the present inventor. The disclosure therein relates to a device and method for qualitative and quantitative analysis of aromatic compounds in water resultant from a Friedel-Crafts Reaction (FCR), more specifically a Lewis-acid catalyzed FCR, for application in a Chemical Reaction Spectrometric (CRS) device or kit. Further, the disclosure therein generally relates to a method whereby a sample to be tested is extracted, the FCR is catalyzed, and the reaction product is analyzed based on the color and intensity thereof to determine aromatic or hydrocarbon components.

The encapsulated reagents of the present disclosure include a linear series of discrete reaction vessels. In this configuration, the encapsulated reaction vessels comprise a tape or strip that is configured for serial or sequential processing of each of the discrete reaction vessels in individual fashion. In exemplary embodiments, the tape or strip may be configured as a roll, a drum, or a coil without limitation, and configurable to unwind during processing of each discrete reaction vessel. In other configurations, the device is configured to manipulate individual discrete reaction vessels. In these configurations, the individually encapsulated reagents include reaction tabs that may be processed by feeding to the device via another apparatus, such as a hopper, or manual insertion by a device operator. In some embodiments, the device for manipulation of the encapsulated reagents is related to the device for analysis.

In exemplary embodiments, the analysis device includes a sample loading device in an analysis compartment. The sample loading device may be configured to expose the encapsulated reagents to a sample fluid and create an encapsulated reaction. In some configurations, the sample loading device is a pressurized loading device, for example, a plunger or piston to selectively permeate a polymeric film of the encapsulated reagents. In other configurations, the sample loading device includes an extension or protrusion configured to at least partially disrupt the polymeric film of the encapsulated reagents and permit the encapsulated reaction.

In exemplary embodiments, the analysis device further includes an optical device. Generally, an optical device includes a light source and a light receiver that are disposed within an analysis compartment. The light source may be an optical probe or emitter such as a laser device or a fiber optic device. Further, the light source may include a filter or other apparatus configured to alter the light properties to irradiate the encapsulated reaction. The light receiver is generally configured to convert the light emitted from the irradiated encapsulated reaction into a graphical format or a data format. Exemplary light receivers may be cameras or photon collecting, counting, or capturing devices and arrays. In some configurations, the light receiver may include a filter, a grating, or another apparatus configured to alter the light properties emitted from the encapsulated reaction.

Referring now to FIG. 1, the present disclosure relates to a reaction device 101 configured for isolating reagents 120. Generally, the reaction device 101 includes a material 102 configurable for the induced, selective, selectively permeable, or semipermeable passage of fluids therethrough. In exemplary configurations, the material 102 is a polymeric material or film. The material 102 includes a non-reactive polymer, and for example, a hydrophobic polymer such that water is at least temporarily excluded from contacting the reagents 120. Exemplary polymers may include polyethylene, polypropylene, other olefinic polymers, or silicon polymers, without limitation.

As discussed hereinabove, the reaction device 101 includes reagents 120 captured by and isolated within the material 102. Generally, the reagents 120 are encapsulated in the material 102 and for example, between a first portion 103 and a second portion 104 of the material 102. The reagents 120 include any reactive material for exposure to an analyte or sample. In some configurations, the reagents 120 may exist as solids or liquids. Generally, the reagents 120 include at least one catalyst, for example a Lewis-acid catalyst. In some configurations, the reagents 120 are a FCR-catalyst. Exemplary catalysts include anhydrous acid catalysts and, more specifically, an anhydrous aluminum chloride ($AlCl_3$). The reagents 120 contain predetermined quantities such as concentrations, masses, or volumes of the catalysts. In certain instances, the reagents 120 include stoichiometric concentrations that are predetermined to sufficiently react with a predetermined volume of an analyte. The reagents 120 are selected for the FCR in order to form chromophores with selected analytes. Thusly configured, the reaction device 101 provides single or multiple regularly spaced, discrete reaction vessels for the reagents 120 in the material 102. The reaction device 101 provides single or multiple discrete analysis vessels for spectrometric analysis.

Figure 2:
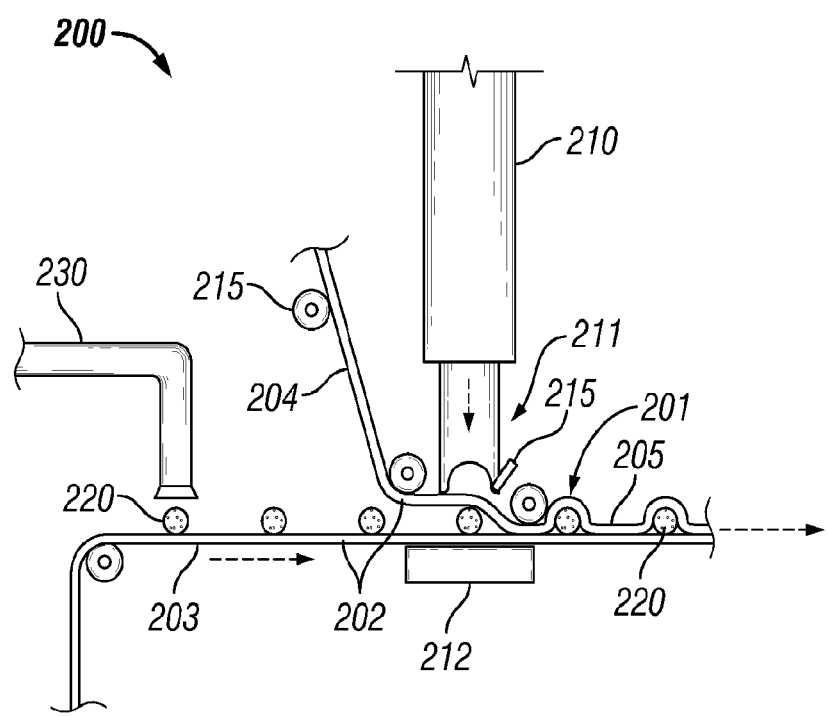
FIG. 2 illustrates a device for manufacturing a reaction device.

Referring now to FIG. 2, a device 200 is illustrated for the manufacturing of a reaction device or devices 201. Generally, the device 200 is configured as a press 210 configurable to create reaction devices 201. In certain instances, the reaction devices 201 are manufactured as a tape 205. Alternatively, the press 210 is configured as a punch, in order to form one or more tabs 206. Tabs 206 may be any configuration of individual or unitary reaction devices 201. In some instances, tabs 206 are planar or approximately planar, having a shape that corresponds to the perimeter of the press 210.

Generally, in either configuration the press 210 includes a sealing surface 211. The sealing surface 211 is any device configured to thermally or pressurably contact and seal a second portion 204 over the reagents 220 and in contact with the surface of the first portion 203. The sealing surface 211 may provide pressure against an arbor or arbor plate 212. The sealing surface 211 may be considered a ring, the diameter of a circle, a cylindrical cross-section, or the outer portion of any 2-dimensional shaped polygon such as a square, triangle, etc., without limitation. Sealing surface 211 may further include elements configured to bond, anneal, vulcanize, or similarly seal the second portion 204 to the first portion 203 of the material 202. Additionally, when the press 210 is configured as a punch, the sealing surface 211 may further include a cutting element such as a blade or a thermal cutting element. In additional configurations, the device 200 may include guides 215 to direct the first portion 203 and the second portion 204 of the material therethrough and to eject the reaction device 201 therefrom. Exemplary guides 215 may be flat surfaces, rollers, tabs, fingers, elastic materials, springs, or other devices that contact the first portion 203, the second portion 204, and the reaction device 201.

Generally, the device 200 further includes a reagent delivery device 230. The reagent delivery device 230 deposits a predetermined quantity of the reagents 220 on the first portion 203. The reagent delivery device 230 operates prior to overlaying the second portion 204, and sealing the reaction device 201 as described hereinabove. Generally, the reagent delivery device 230 may be a programmable or automated device, for example an auto-pipetting device or similar. In solids handling instances, the reagent delivery device 230 may be a volumetric or gravimetric delivery system, or a vacuum-solids deposition system in alternative embodiments. In some configurations, the reagent delivery device 230 may be operated manually, for example by manufacturing personnel in order to remain flexible with respect to the reagent delivery or deposition.

Figure 3:
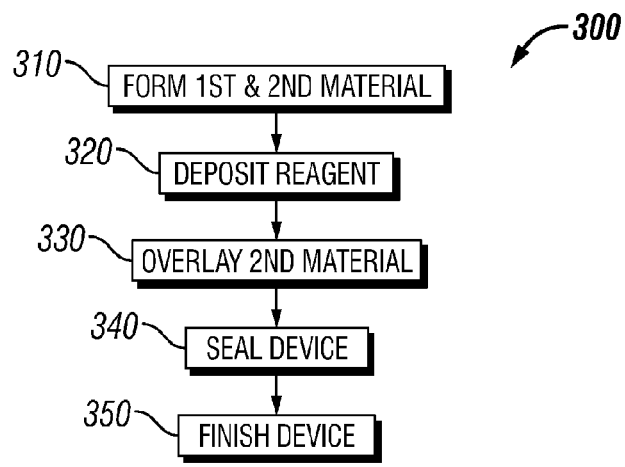
FIG. 3 illustrates a flow chart schematic for manufacturing a reaction device.

Still referring to FIG. 2, the reaction device 201 is constructed by a method 300 illustrated in FIG. 3. As shown in FIG. 3, the method 300 includes the steps of forming 310 a first and second portion of a material, depositing 320 a reagent on a first portion of the material, overlying 330 a second portion of material, sealing 340 the reagent to form a reaction device, and finishing 350 the reaction device. Forming 310 a first and second portion of the material may include extruding or depositing a polymeric material as described previously to form a film. Depositing 320 a reagent on a first portion of the material includes placing a drop of a fluid or a portion of solids on a supporting layer of the polymeric film. Overlying 330 a second portion of the material includes covering the reagent with a second portion of the polymeric material, generally the same material, and subsequently sealing 340 the reagent to form a reaction device, including capturing and isolating the reagent. The step of finishing 340 the reaction device includes producing a reagent device linear array or tape, or in certain instances, punching or pushing out tabs from a sealed polymeric material.

Figure 4:
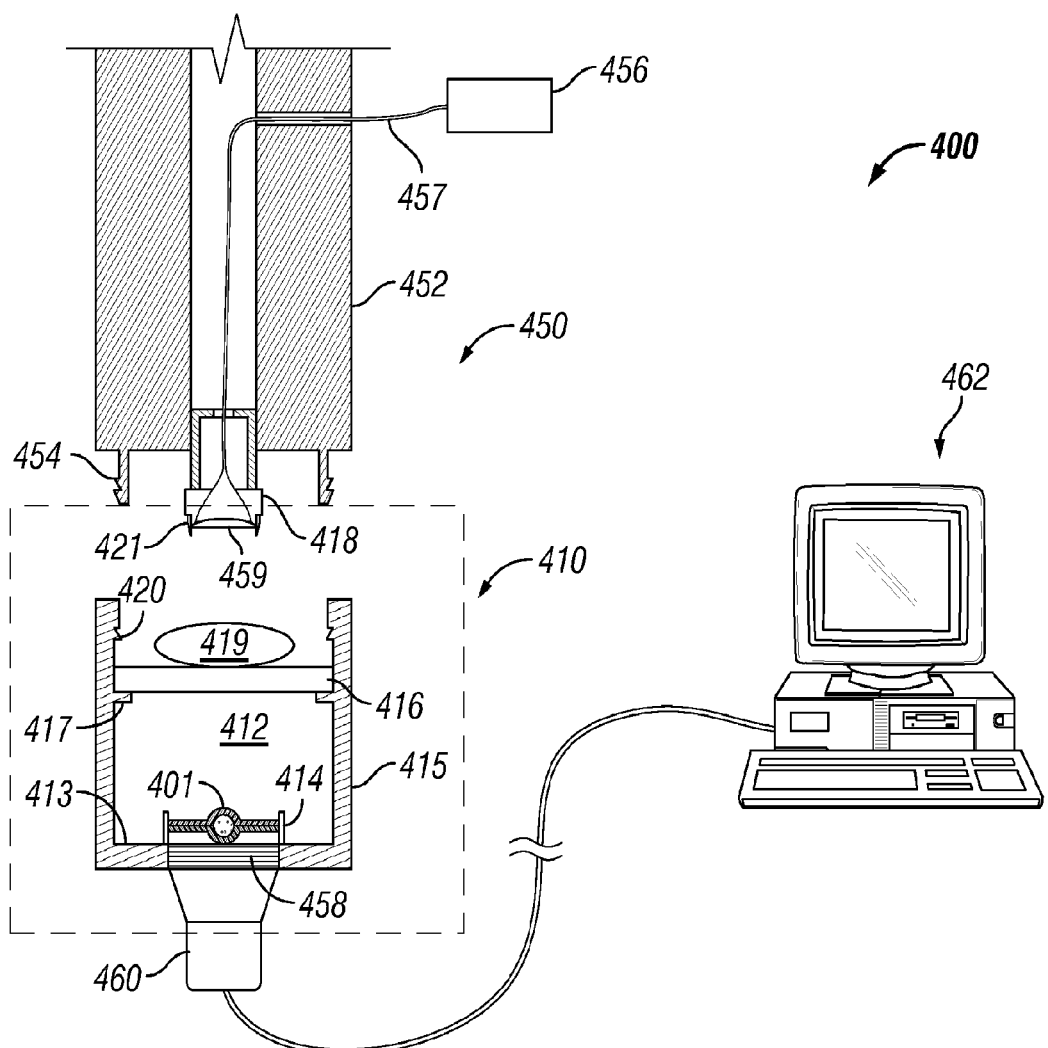
FIG. 4 illustrates a device for analyzing hydrocarbons in soil and water.

Referring now to FIG. 4, the present disclosure relates to an analysis device 400. Analysis device 400 is generally configured to utilize at least one reaction device 401 to analyze a sample of hydrocarbons. The analysis device 400 includes a chemical module 410 and an optical module 450. The chemical module 410 includes a liquid reaction chamber or extraction chamber 412, a reaction device support 414, a solvent reservoir 416, an injector 418, and a coupler 420. The optical module 450 includes a housing 452, a coupler 454, a light source 456, a filter 458, a receptor 460 and a graphical analysis device 462.

The extraction chamber 412 of the analysis device is configured as a vessel for extracting hydrocarbons and aromatics as analytes from an environmental material, geological material, soil, and/or water sample. The extraction chamber 412 includes any material that is resistant to acid, solvent, hydrocarbon, or other reactive chemical groups, such as alkanes or halides thereof. In certain instances, the extraction chamber 412 is constructed out of poly-vinyl chloride (PVC) or a comparable material. The extraction chamber 412 is generally constructed or configured to retain a liquid sample. The extraction chamber 412 includes a floor 413 and a wall or walls 415 disposed about the perimeter. The floor 413 of the extraction chamber 412 includes a reaction device support 414. In certain instances, the extraction chamber 412 is configured to be disposable or rapidly replaceable, such as a modular component.

Reaction device support 414 is configured to retain or guide the reactive device 401 in the extraction chamber 412. In exemplary embodiments, the reaction device support 414 includes a recess, a protrusion, a clamp, or any similar modification or addition to the floor 413 of the extraction chamber 412 to retain a tab-configured reaction device 401. In alternative instances, the reaction device support 414 includes a track, a guide, or other directional modification for permitting placement or localization of a portion of a tape-configured reaction device 401 in the extraction chamber. In these instances, the floor 413 may be sealably connected to the walls 415 of the reaction chamber, such that at least partial de-coupling thereof permits a tape-configured reaction device to be inserted and pulled or otherwise manipulated through the extraction chamber. Further, the floor 413 and reaction device support 414 include an optical window or connector.

The walls 415 include the coupler 420 configured as any mechanical interaction such as a snap-fit, an interference-fit, or threadable connector. In certain configurations, the walls 415 may have additional supports 417 configured as rings, tabs, or lips. The supports 417 are configured to support a solvent reservoir 416.

The solvent reservoir 416 includes a partially or totally sealable vessel for retaining a predetermined volume, mass, or concentration of a reaction solvent. Generally, the solvent reservoir 416 may be configured to be resistant to any material that is resistant to acid, solvent, hydrocarbon, or other reactive chemical groups, such as alkanes or halides thereof. In certain instances, the solvent reservoir 416 is constructed out of poly-vinyl chloride (PVC), polyethylene (PE), polypropylene (PP) or a comparable material. Alternatively, the solvent reservoir 416 may be constructed out of thin metallic or metallic alloy films, such as aluminum. The solvent reservoir 416 may include a packet or sealed volume that is puncturable or frangible. In some configurations, the solvent reservoir 416 may include a tab or opening configured to puncture or fail under an induced condition. Further, the solvent reservoir 416 may be configured as a liquid volume transferring or releasing device, such as a pipet, pump, piston, or syringe. In other configurations, solvent reservoir 416 includes sample site 419. Sample site 419 includes a depression or cup in the surface of the solvent reservoir shape. The sample site 419 is configured to receive and retain a sample to be analyzed prior to the extraction of the analytes.

The injector 418 is configured to disrupt, puncture, pierce, inject, or otherwise evacuate the solvent reservoir 416. The injector 418 may include features 421 such as prongs, points, or serrations in order to mechanically compromise the solvent reservoir 416. The injector 418 further promotes the mechanical mixing or contacting of the sample from sample site 419 and the solvent from solvent reservoir 416. In certain instances, the injector 418 is configured as a plunger or a piston for extending from the optical module 450 housing 452 towards the floor 413 of the extraction chamber 412. Also, the injector 418 may be configured to propel the solvent from the solvent reservoir 416. In further configurations, the injector 418 initiates the sample extraction reaction and the exposure of the extracted analyte to the FCR catalysts The optical module 450 includes components of the analysis device peripheral to and in communication with the extraction chamber 412. Generally, the peripheral components relate to optical analysis of the FCR products. The optical module 450 includes a housing 452 having a respective or complementary coupler 454 disposed exteriorly. The coupler 454 is configured for interacting with the coupler 420 of the extraction chamber 412 on the chemical module 410. The housing 452 includes an elongate hollow body through which the injector 418 passes. The injector 418 is configurable to move along the elongate axis of the housing 452 in extension and refraction modes, for example as a plunger or piston.

Light source 456 may be a separate or integral component of housing 452. Light source 456 is configured as a halogen or tungsten halogen light source having a broad emission spectrum. Light source 456 may further include other known emissive configurations for projecting excitation light and, in some instances, predetermined wavelengths of light, onto a reaction device 401. Additionally, the light source 456 may be configured to emit or have emitted light pass through the housing 452 and in some configurations the injector 418. The light source 456 may include a plurality of optic bundles, pipes, or fibers 457 that extend along the elongate axis of the housing 452 to at least one lens 459 proximal to the injector 418. In certain instances, there is a plurality of fibers 457 extending from the light source 456 to the lens 459. Further, the fibers 457 or the lens 459 may include a light pipe that extends around the circumference of the injector 418.

Disposed in or adjacent to the floor 413 of the extraction module 410 there is a filter 458. The filter 458 is disposed adjacent to and in the light path of light refracted, transmitted or emitted during chromophore absorbance. The filter 458 includes an optical filter, such as but not limited to a polarizer, a diffraction grating, a chromatic or dichroic lens, or any other optical filter configurable to alter light refracted or transmitted through the sample. In certain instances, the filter 458 may be an electronic device for optical analysis or integral to the receptor 460.

The receptor 460 includes an optical array for collecting photons that pass through the filter 458. Exemplary receptor 460 configurations include cameras, charge coupled devices (CCDs), spectrometers, or mini-spectrometers. The receptor 460 generates a digital output that is conveyed to a graphical analysis device 462 such as a computer. Without limitation by theory, the graphical analysis device 462 includes a processor configured to access instructions stored on a memory, such that when executed, the manipulation, analysis, display, and reproduction of graphical data indicative of the photons impingent on the receptor 460 is possible. In some instances, the graphical analysis device may be a hard drive or portable processing/storage medium. In other instances, the receptor 460 is configured for reversible coupling to the extraction chamber 412, for example via SubMiniature A (SMA) connectors or other coaxial connectors.

Figure 5:
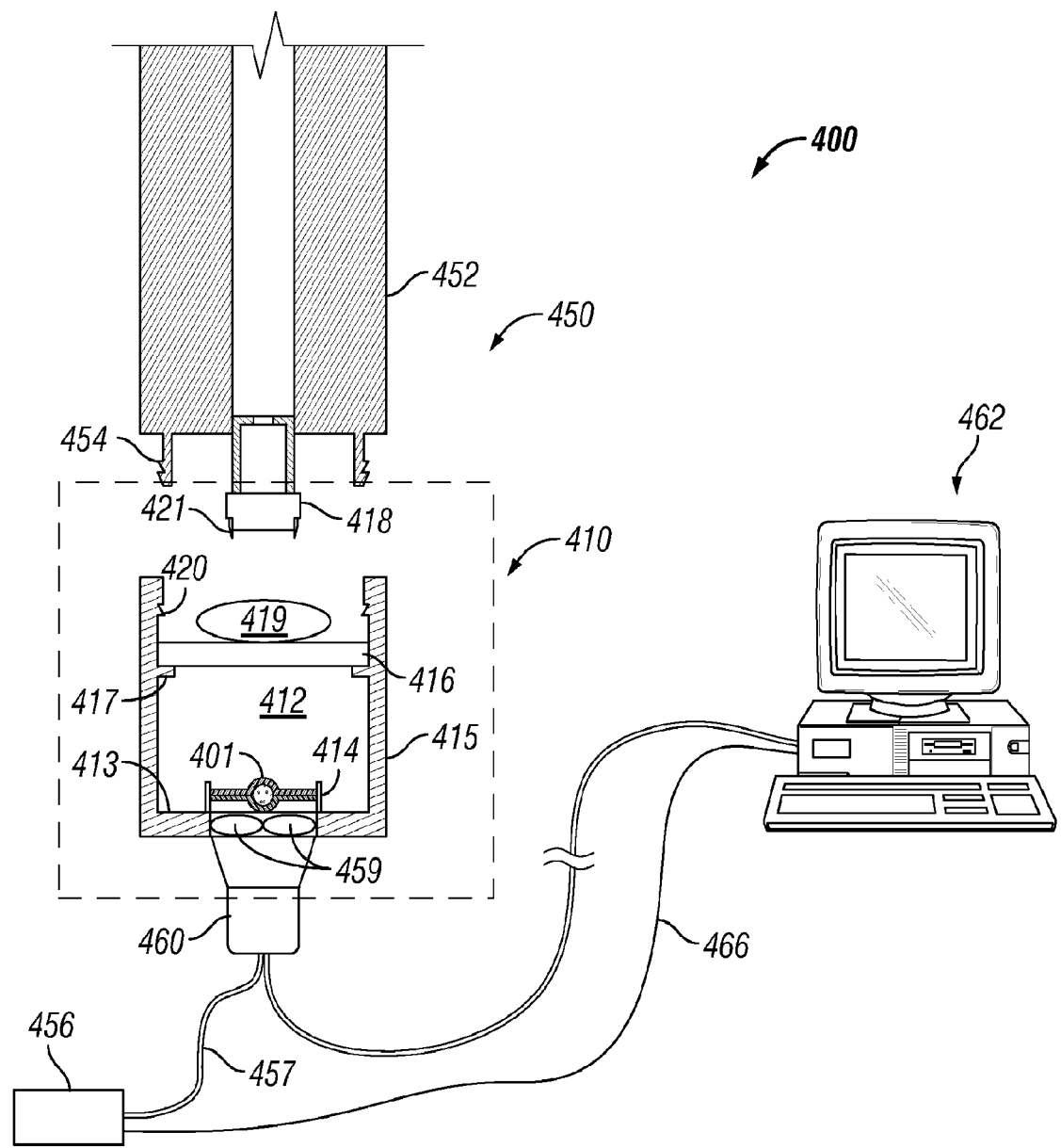
FIG. 5 illustrates an alternate configuration for analyzing hydrocarbons in soil and water.

Referring now to FIG. 5, there is illustrated an alternative configuration of the device 400 described herein. In the present configuration, the light source 456 including fibers 457 and lenses 459 illuminate the reaction device 401 from adjacent the floor 413 of the extraction chamber 412 in the chemical module 410. Thusly configured, the lens 459 and filter 458 may be monolithic or unitary components. Still further, the lens 459 and filter 458 may include a dichroic structure, such that the wavelengths of the light used for illumination is in a specific range of wavelengths and the refracted or transmitted light collected at the receptor is in a separate, discrete range of wavelengths. Without limitation by theory, configured thusly the device 400 may be more compact and transportable.

Further, in some configurations, the light source 456 is in communication with the graphical analysis device 462 by a communication link 466. The communication link 466 may permit the changing and control of the illumination wavelengths from the light source 456; alternatively, communication link 466 permits activation and analysis simultaneously. In certain instances, the light source 456, receptor 460, and graphical analysis device 462 are components of the same device.

Figure 6:
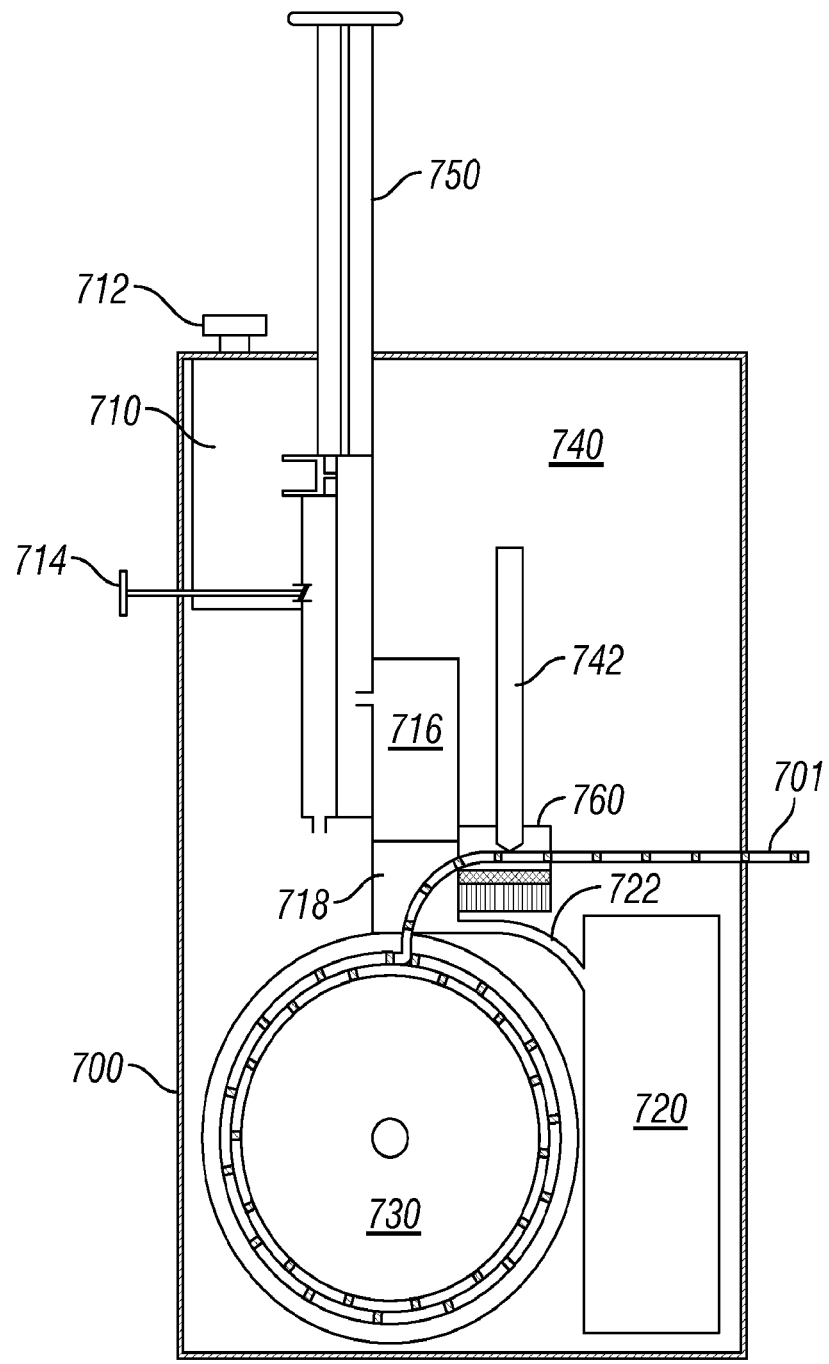
FIG. 6 illustrates another alternate configuration for analyzing hydrocarbons in soil and water.

Referring now to FIG. 6 there is illustrated a further configuration of the present disclosure. Generally, the device 700 illustrated includes a completely self-contained device for the analysis of hydrocarbons in soil or water samples. In the present configuration, the device 700 includes a housing 711 wherein the housing includes at least four chambers or modules. The housing 711 includes a sample chamber 710, a waste chamber 720, a reaction device storage 730, and an analysis device chamber 740. The chambers 710, 720, 730, 740 are in communication via fluid and materials conduits. The fluid conduits include a dual channel or dual pass plunger 750.

Thusly configured, the sample chamber 710 includes a sample conduit 712 for inserting or injecting and fluidizing a sample therein. Further, the sample chamber includes an exit valve 714 in fluid connection with the plunger 750. The plunger 750 is in fluid connection with the solvent reservoir 716 and the reaction chamber 718. From the reaction device chamber 730 a portion of at least one reaction device 701 contacts the fluid in the reaction chamber 718. The remaining solvent and analyte is withdrawn from the reaction chamber 718 to the waste chamber 720 via a drain or other vessel. The at least one reaction device 701 is conveyed to the analysis chamber 740. In the analysis chamber 740 the reaction device 701 is illuminated by the probe 742, such that a spectrometer 760 may collect the refracted or transmitted light.

Figure 7:
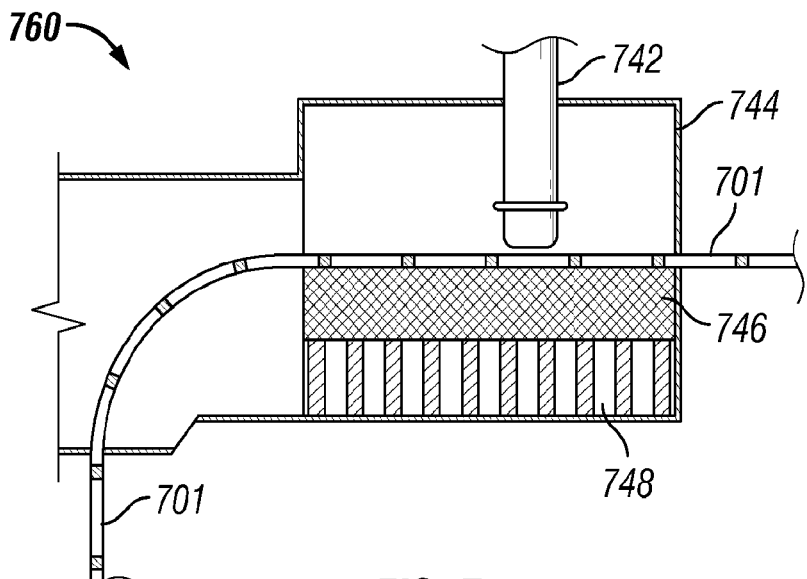
FIG. 7 illustrates a spectrometer configuration for analyzing hydrocarbons in soil and water.

Referring now to FIG. 7, there is illustrated an exemplary spectrometer 760. Generally, the spectrometer includes a probe 742 that extends into an analytical compartment 744 for the illumination of the sample in the reaction device 701. Further, the spectrometer 760 generally includes a diffraction grating or similar filter 746 and a receptor 748. Suitable exemplary filters 746 and receptors 748 have been described hereinabove. In some configurations, the spectrometer may be a mini-spectrometer such as but not limited to those produced by Hamamatsu.

In operation of the configuration shown in FIGS. 6 and 7, the first step includes: liquid or solid samples are introduced into the sample extraction chamber 710 via the sample access 712. Subsequently, withdrawal of the dual channel syringe 750 causes a small aliquot of the extraction solvent from the solvent reservoir 716 to inject into the sample extraction chamber 710. Further, depression of the syringe and simultaneous pressing of the SEC manual valve 714 causes the aliquot of the sample and solvent to be injected by the left-hand channel of the syringe from the extraction chamber into the extract/catalyst reaction chamber (ECRC) 718. Electronic activation (not shown) of the motorized catalyst tape storage disc drum in the reaction device chamber 730 causes one segment of the catalyst tape 701 to advance, thereby positioning a catalyst packet under the light probe 742 for measuring absorbance. Still further, electronic activation of the light probe 742 also activates the spectrometer 760, which causes a digital signal to be sent to the computer (not shown) via the USB port (not shown), for example. Manual depression of the ECRC valve drains the extract into the extract waste storage reservoir 722.

Figure 8:
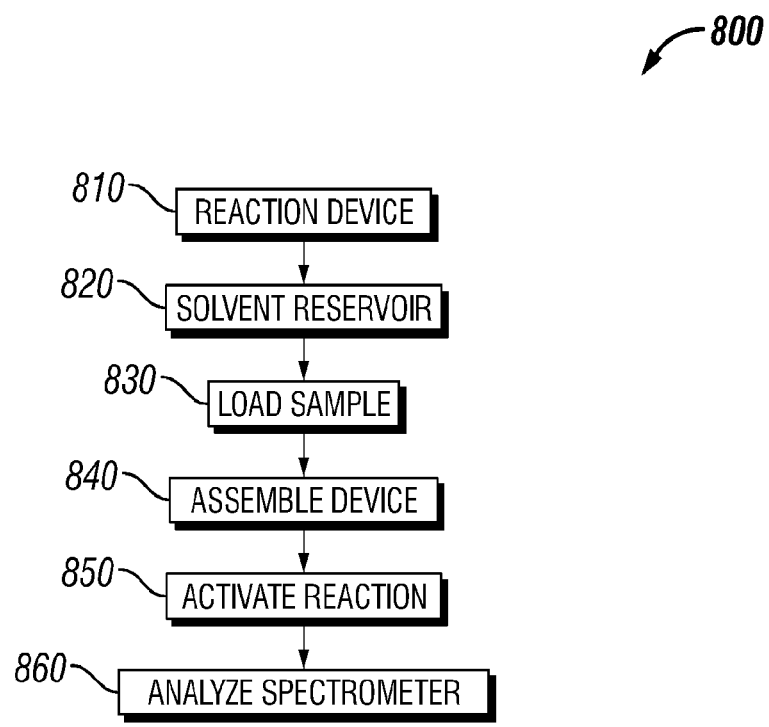
FIG. 8 illustrates a flow chart schematic for a method of analyzing hydrocarbons in soil and water.

Referring now to FIG. 8 there is illustrated a method 800 for conducting an analysis according to the device illustrated in FIGS. 4 and 5. In instances, the method includes preparing 810 the reaction device, positioning 820 the solvent reservoir, loading 830 the sample or analyte, assembling 840 the analysis device, activating 850 the extraction and FCR process, and analyzing 860 the FCR products by a spectrometer. In certain instances, preparing 810 the reaction device includes inserting manually or automatically a reaction device into the extraction chamber, wherein the reaction device includes a Friedel-Crafts catalyst. Activating 850 the extract and FCR process includes mixing the sample, the extraction solvent, and the Friedel-Crafts catalyst to attach a chromophore to aromatics and hydrocarbons in the analyte. Also, analyzing 860 the FCR product(s) includes illuminating the reaction device with a light source, such as a metal halide, and measuring the absorbance of the transmitted light.

Referring now to FIG. 9, there is illustrated another configuration of an analysis device 900 as described herein for FIG. 4. In the present configuration, the analysis device 900 generally utilizes at least one reaction device 901 to analyze a liquid sample 919 of hydrocarbons. The analysis device 900 includes a chemical module 910 and an optical module 950. The chemical module 910 includes a liquid reaction chamber or extraction chamber 912, a reaction device support 914, a solvent reservoir 916, an injector 918, and a coupler 920. The optical module 950 includes a housing 952, a coupler 954, a light source 956, a receptor 960 and a graphical analysis device 962.

The analysis device 900 includes a housing 952 that is reversibly connected to the extraction chamber 912. The extraction chamber 912 includes a reaction device support 914 that may be configured as previously described or functions as a receptor or indentation in the floor 913 of the extraction chamber 912. Further, the receptor 960 may be threadably engaged or otherwise coupled to the extraction module and passing through the floor 913 in order to optically analyze the reaction device 901.

The housing 952 includes the solvent reservoir 916 and an injector 918 configured to evacuate solvent or reagents therefrom. In instances, the solvent reservoir 916 and injector 918 are configured as a pump or piston, such as a syringe, in order to deliver solvent to the extraction chamber. The solvent reservoir and injector 918 may be coaxial with an elongate axis A of the analysis device 900. Further, the housing 952 retains the light source 956 that may be arranged adjacent to or parallel with the solvent reservoir 916. In certain instances, the light source 956 contains a power supply 957 in order to retain a compact or portable shape.

Thusly configured, the analysis device 900 permits the insertion of a reaction device 901 into the holder 914 prior to the addition of the sample 919 into the extraction chamber 912. Subsequently, the extraction chamber 912 is coupled to the housing 952. The injector 918 evacuates the reservoir 916 into the sample 919 in the chamber 912. After a predetermined period of reaction, the light source 956 may be activated concurrently with the receptor 960 and the graphical analysis device 962.

The present disclosure is based on the generation of robust, transient chromophores generated by sigma and pi electrons that engage in bond formation in Friedel-Crafts reactions. These chromophores resonate with frequencies in the near ultraviolet (UV) and visible (Vis) portions of the electromagnetic spectrum generated by a tungsten/halogen energy source. In the present method and apparatus a soil, water, or formation fluid sample is extracted with an alkyl halide extractant, such as but not limited to carbon tetrachloride. The extract solution is then caused to undergo Friedel-Crafts (FC) reactions by exposure to a Lewis-acid catalyst such as but not limited to anhydrous Aluminum Chloride. This disclosure describes the apparatus that can accept the sample(s), the extraction solvent, a means for introducing the sample(s) and solvent into an extraction chamber, a means for presenting a precise amount of the catalyst to the extracted sample solution, a tungsten/halogen source, and a charge-coupled-device (CCD) spectrometer for the detection of the signal generated by the FC-produced chromophores.

The disclosure operates by introducing a sample (soil, water, or formation fluid) via the sample access into the sample extraction chamber using the dual channel syringe. The syringe is equipped with valves that regulate the flow of solvent from the solvent reservoir into the syringe and, subsequently, into the ECRC. The catalyst tape is fed into the ECRC by the motorized catalyst tape storage drum, for example. After a precise time and extraction temperature, which determine the diffusion of the solvent extract into the polyethylene-enclosed catalyst, the chromophoric signal is read by the CCD spectrometer. The digitized signal from the CCD is electrically transmitted via a standard USB connection from the electronic module to a computer or other microprocessor-based read-out device.

The embodiment described is designed as a small-sized device such that it can be easily transported to the field and utilized manually by one person for soil or water analysis for petroleum contamination. Conversely, this small device can be fully automated with appropriate electronic operation of the syringe and valving, and utilized with appropriate thermal and vibration insulation as a downhole wireline device for oil exploration purposes (geological formation fluid analysis).

Many modifications and variations, particularly in regard to automated or remote actuation, as specifically mentioned in the embodied device and method may be made without departing substantially from the concept of the present disclosure. Accordingly, it should be clearly understood that the form of the disclosure described herein is exemplary only, and is not intended as a limitation on the scope thereof.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented. Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A reaction device comprising:
a first portion of a permeable material; and
a second portion of the permeable material sealed against the first portion to sealably encapsulate an anhydrous Friedel-Crafts catalyst;
wherein the reaction device is configured for reacting with a sample extract in a Friedel-Crafts reaction such that the sample extract permeates through the permeable material to contact the anhydrous Friedel-Crafts catalyst encapsulated by the first and second portions and thereby cause the Friedel-Crafts reaction.

2. The device of claim 1, wherein the first and second portions of the permeable material are configured to form a linear tape comprising regularly spaced discrete reaction vessels retaining the Friedel-Crafts catalyst or a tab comprising individual vessels retaining the Friedel-Crafts catalyst.

3. The device of claim 1, wherein the first and second portions of the permeable material comprises at least one non-reactive polymer chosen from the group consisting of olefinic polymers, silicon polymers, or hydrophobic polymers.

4. A method of manufacturing a reaction device comprising positioning an anhydrous catalyst reagent on a first portion of a permeable material;
overlaying a second portion of a permeable material;
sealing the second material to the first material to encapsulate the anhydrous catalyst reagent and finish the reaction device; and
exposing the encapsulated reaction device to a sample extract to cause a Friedel-Crafts reaction between the sample extract and the anhydrous catalyst reagent.

5. The method of claim 4, wherein the anhydrous catalyst comprises a Friedel-Crafts catalyst.

6. The method of claim 4, wherein the material comprises at least one non-reactive polymer chosen from the group consisting of polyethylene, polypropylene, other olefinic polymers, silicon polymers, or hydrophobic polymers.

7. The method of claim 4, wherein sealing the second material to the first material comprise thermal sealing or pressure sealing.

8. The method of claim 4, wherein finishing the encapsulated reaction device comprises forming a linear tape having regularly spaced discrete reaction vessels retaining the Friedel-Crafts catalyst or forming individual, discrete tabs retaining the Friedel-Crafts catalyst.

9. A device for analyzing soil and water contaminants comprising:
a chemical module, wherein the chemical module comprises an extraction vessel having a floor configured to retain a reaction device, walls configured to retain a solvent reservoir and a coupler; and
an analysis module, wherein the analysis module comprises a body with a complementary coupler for releasably coupling with the coupler of the chemical module, a light source, a filter, an optical receptor, and an analysis device;
wherein, when the coupler of the chemical module is releasably coupled with the coupler of the analysis module, relative movement between the chemical module and the analysis module is restricted.

10. The device of claim 9, wherein the reaction device comprises a first and a second portion of a permeable material encapsulating a Friedel-Crafts catalyst.

11. The device of claim 10, wherein the first and second portion of the permeable material are configured to form a linear tape having regularly spaced discrete reaction vessels retaining the Friedel-Crafts catalyst or individual, discrete tabs retaining the Friedel-Crafts catalyst.

12. The device of claim 10, wherein the first and second portion of the permeable material comprises at least one non-reactive polymer chosen from the group consisting of polyethylene, polypropylene, other olefinic polymers, silicon polymers, or hydrophobic polymers.

13. The device of claim 9, wherein the solvent reservoir further comprises a sample site.

14. The device of claim 13, wherein the body further comprises an extendible plunger configured to mechanically mix a solvent and a sample by disrupting the solvent reservoir to form an extract.

15. The device of claim 14, wherein the plunger is configured to expose the reaction device to the extract.

16. The device of claim 15, wherein the reaction device is configured to catalyze a Friedel-Crafts chromophore reaction in the extract.

17. The device of claim 9, wherein the light source comprises a metal halide configured for illuminating the extract in a spectra of the Friedel-Crafts chromophore.

18. The device of claim 9, wherein the receptor comprises an optical receptor configured for detecting the refracted or transmitted light in the extract.

19. A method for analyzing soil and water contaminants comprising:
loading a reaction device having a Friedel-Crafts catalyst encapsulated in a permeable material;
positioning a solvent reservoir adjacent the reaction device;
piercing a barrier of the solvent reservoir to leak solvent from the solvent reservoir to mix a sample with solvent from the solvent reservoir to form an extract;
exposing the extract to the reaction device to form a Friedel-Crafts chromophore in the extract;
illuminating the extract;
collecting the refracted or transmitted light therethrough; and
generating a spectrogram indicative of the soil and water contaminants.

20. The device of claim 9, wherein the analysis module comprises a prong for piercing a barrier of the solvent reservoir of the chemical module.

* * * * *